United States Patent
Caroll-James

(10) Patent No.: US 9,931,560 B2
(45) Date of Patent: Apr. 3, 2018

(54) SHADOW GLOVES

(71) Applicant: H. Carnell Caroll-James, Dover, DE (US)

(72) Inventor: H. Carnell Caroll-James, Dover, DE (US)

(*) Notice: Subject to any disclaimer, the term of this patent is extended or adjusted under 35 U.S.C. 154(b) by 0 days.

(21) Appl. No.: 14/979,286

(22) Filed: Dec. 22, 2015

(65) Prior Publication Data

US 2016/0175683 A1   Jun. 23, 2016

Related U.S. Application Data

(60) Provisional application No. 62/095,465, filed on Dec. 22, 2014.

(51) Int. Cl.
| | |
|---|---|
| A63F 9/24 | (2006.01) |
| A63B 71/06 | (2006.01) |
| A63B 71/14 | (2006.01) |
| A61B 5/11 | (2006.01) |
| A61B 5/00 | (2006.01) |
| A63B 24/00 | (2006.01) |

(52) U.S. Cl.
CPC ............... *A63B 71/06* (2013.01); *A61B 5/11* (2013.01); *A61B 5/6806* (2013.01); *A63B 71/145* (2013.01); *A61B 2503/10* (2013.01); *A63B 24/0062* (2013.01)

(58) Field of Classification Search
None
See application file for complete search history.

(56) References Cited

U.S. PATENT DOCUMENTS

| | | | | |
|---|---|---|---|---|
| 8,187,097 | B1* | 5/2012 | Zhang | A63F 13/52 463/37 |
| 2005/0014542 | A1* | 1/2005 | Ueshima | A63F 13/02 463/8 |
| 2009/0117958 | A1* | 5/2009 | Ueshima | A63F 13/10 463/8 |
| 2011/0234483 | A1* | 9/2011 | Lan | G06F 3/014 345/156 |
| 2013/0128022 | A1* | 5/2013 | Bose | H04N 7/18 348/77 |

\* cited by examiner

*Primary Examiner* — Paul A D'Agostino

(57) ABSTRACT

A method for analyzing punching activities of a boxer during a training session is implemented through a glove that is worn by the boxer. The glove includes a microprocessor, an inertial measurement unit, and other related electrical components so that the method of analyzing punching activities can be executed through a single punch analysis. The inertial measurement unit timestamps and collects raw orientation and spatial positioning data for the glove, and enables the microprocessor to execute the single punch analysis throughout the training session. The single punch analysis outputs and displays a forward glove speed, a forward glove force, a forward glove power, heart rate of the boxer, calories burned by the boxer, lag time between multiple punches, and total number of punches throughout the training session.

10 Claims, 12 Drawing Sheets

SHADOW GLOVES

The current application claims a priority to the U.S. Provisional Patent application Ser. No. 62/095,465 filed on Dec. 22, 2014.

FIELD OF THE INVENTION

The present invention relates generally to a method of data analyses for fitness and athletic training. More specifically, the present invention is a pair of modified gloves that includes multiple sensors and display screens to enable the user to track the number of punches thrown during a workout or training session, as well as the force at which each punch is thrown and other related data analyses.

BACKGROUND OF THE INVENTION

Since boxing oriented workout or training session involves forceful and repetitive punching, precautions must be taken to prevent damage to bones in the hand. Most trainers do not allow boxers to train and spar without wrist wrap and boxing gloves. The wrist wraps are used to secure the bones in the hand, and the boxing gloves are used to protect the hands from blunt injury, allowing boxers to throw punches with more force than if they did not utilize them. However, the existing wrist wraps and the boxing gloves do not tracking the number of punches thrown and any other types of endurance data during the workout or training session. The number of punches thrown and types of endurance data provide valuable information as to the quality of the workout so that the trainers are able to identify weakness and different training patterns of the boxers. These information can be helpful to the trainers so that the trainers can target the areas that need to be improved while monitoring the health of the boxer.

It is an objective of the present invention to provide a method of analyzing punching activities of a boxer during a training session. The present invention is carried out through a pair of modified gloves that can provide statistical and endurance data. The pair of modified gloves includes multiple sensors and display screens to enable the user to track the number of punches thrown during a workout or training session, as well as the force at which these punches are thrown. The gloves would also indicate other related data analyses such as, the time elapsed in between punches, the number of calories burned from the workout session, and heart rate monitoring during the workout session.

DETAIL DESCRIPTIONS OF THE INVENTION

All illustrations of the drawings are for the purpose of describing selected versions of the present invention and are not intended to limit the scope of the present invention.

Figure 1:
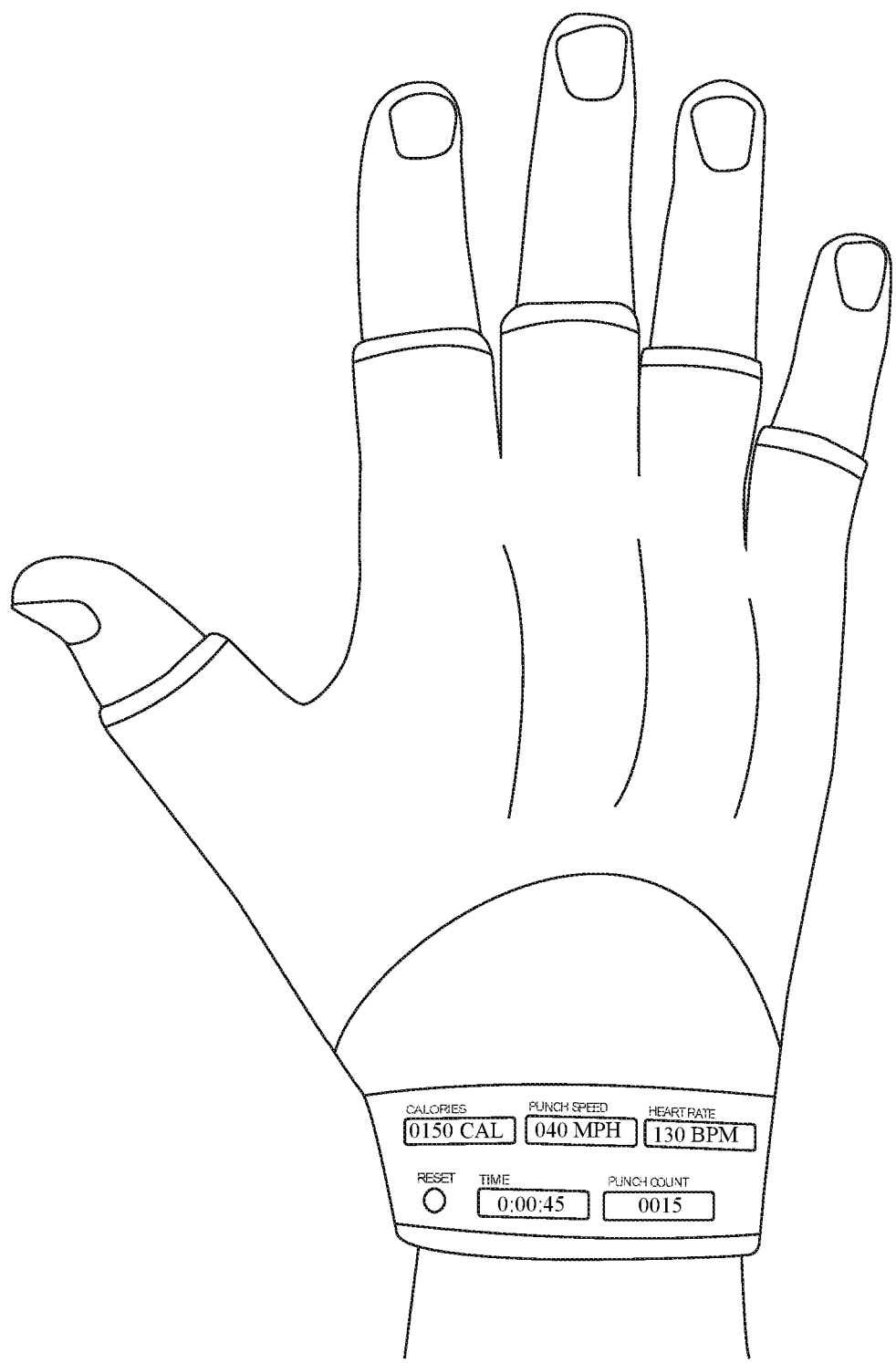
FIG. 1 is a perspective view of the glove that the present invention is implemented.
Figure 2:
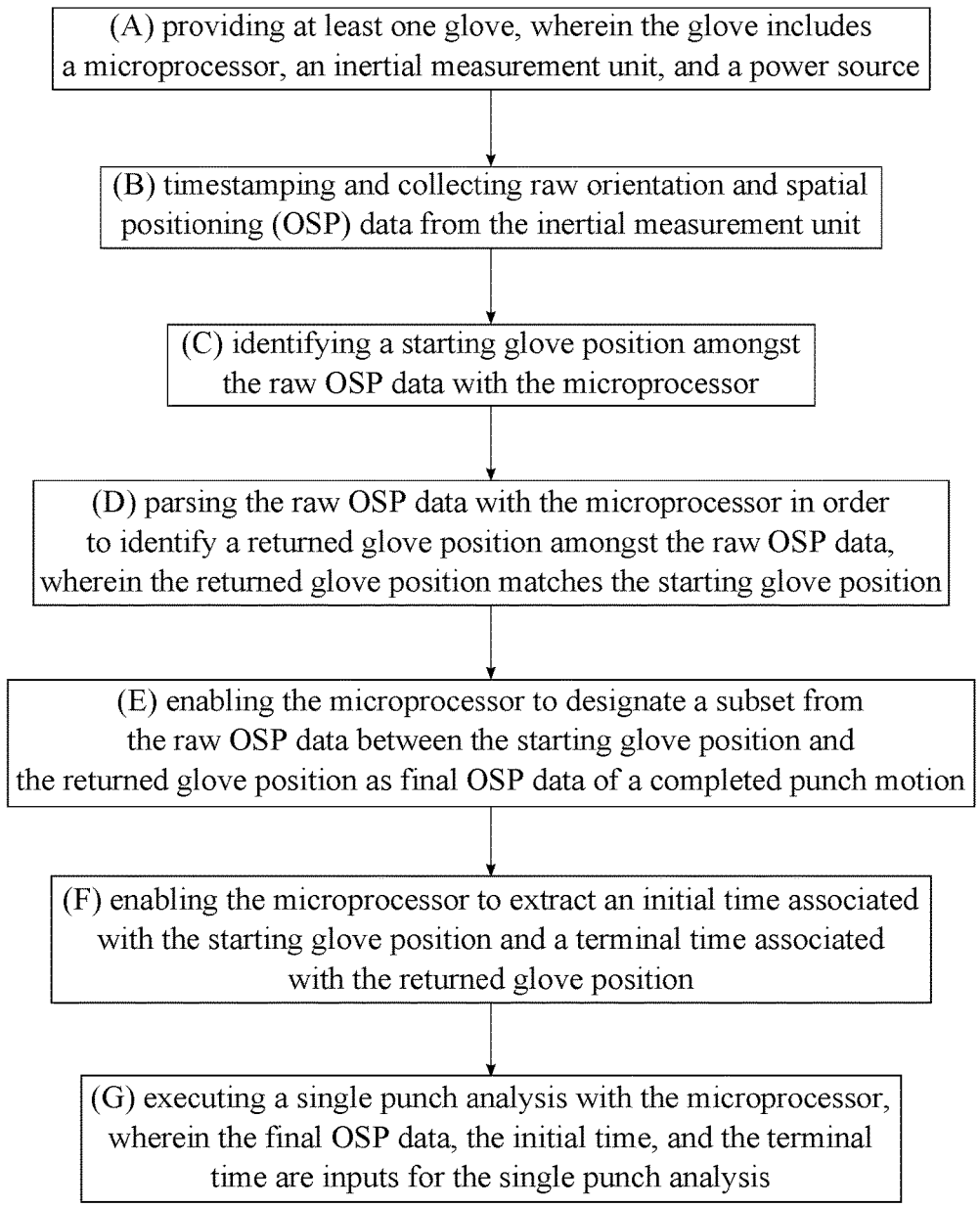
FIG. 2 is a flow chart illustrating the basic overall process of the present invention.
Figure 3:
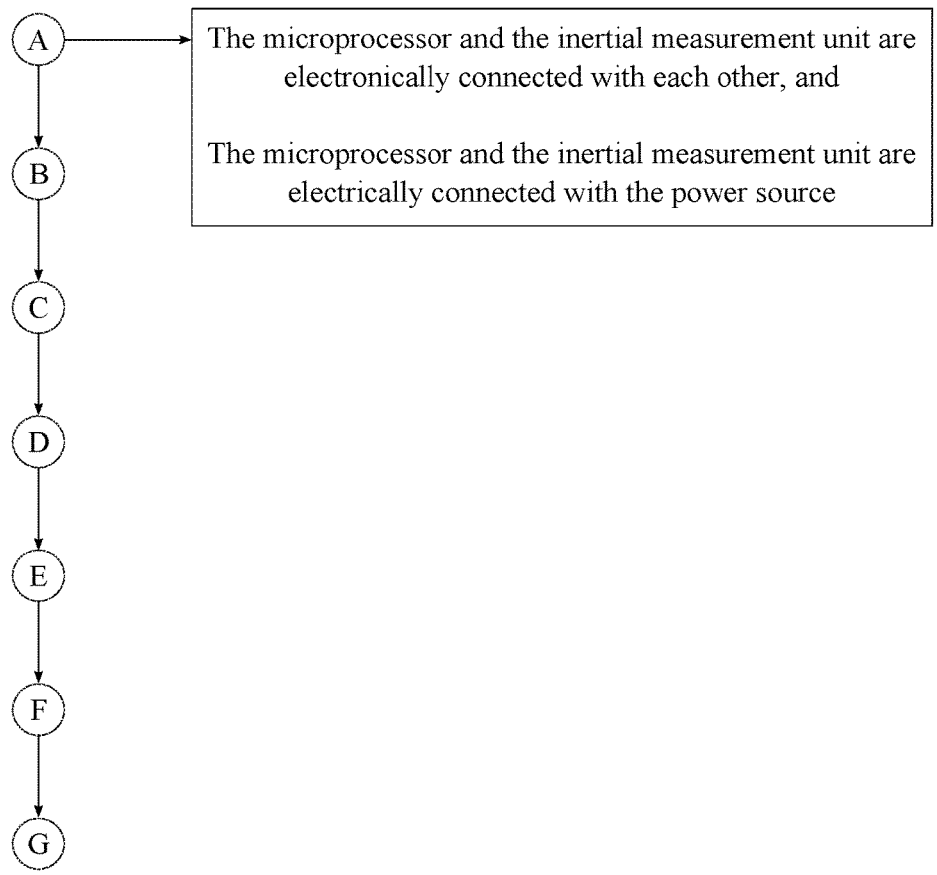
FIG. 3 is a flow chart illustrating the electronical and electrical connection of the present invention within the overall process.

In reference to FIG. 1-3, the present invention is a method for analyzing punching activities of a boxer during a training session. In order to implement the present invention, the boxer has to wear at least one glove. In order words, the boxer can wear a single glove or a pair of gloves during the training session. The glove comprises a microprocessor, an inertial measurement unit, a power source, a weight sensor, an on/off button, and at least one display screen so that the present invention can be processed within the glove. The microprocessor is electronically connected with the inertial measurement unit, the weight sensor, and the display screen to process the present invention while the power source electrically powers the inertial measurement unit, the weight sensor, and the display screen through the on/off button. The boxer is visually able to engage with the glove through the display screen as outputs of the present invention are displayed to the boxer. The glove can be configured as a fully enclosed glove or a fingerless glove as the both different types are able to implement the present invention. Furthermore, the display screen can function as a touchscreen so that the boxer is able to efficiently engage with the glove during the training session. In reference to the fully enclosed pair of gloves, the touchscreen of the first glove can be operated without having to take off the second glove as each of the finger sleeves of the pair of gloves is integrated with a touch screen compatible conductive coating. Since the fingerless glove exposes the fingers of the boxer, the touch screen can be easily operated through the boxer's fingers.

In reference to FIG. 2, when the boxer is ready to begin the training session, the glove can be activated through the on/off button to initiate the present invention. Then the inertial measurement unit starts collecting and timestamping raw orientation and spatial positioning (OSP) data of the glove. As a result of the collected and timestamped raw OSP data of the present invention, the microprocessor is able to identify a starting glove position amongst the raw OSP data. The starting glove position is recognized as a pre-punch position of the glove as the boxer gets ready to launch a punch. Once the punch is launched, the inertial measurement unit continuously collects and timestamps the raw OSP data throughout the punching process. Then the microprocessor parses through the raw OSP data in order to identify a returned glove position amongst the raw OSP data. The returned glove position is recognized as a post-punch position of the glove. The inertial measurement unit is able to determine and confirm the returned glove position within the present invention as the returned glove position matches with the starting glove position.

The microprocessor then designates a subset from the raw OSP data between the starting glove position and the returned glove position as final OSP data of a completed punch motion. More specifically, the completed punch motion begins with the starting glove position and ends with the returned glove position to separate the final OSP data from the raw OSP data. The microprocessor is then able to extract an initial time, which is associated with the starting glove position, through the timestamping process of the raw OSP data. The microprocessor then extracts a terminal time from the timestamping process of the raw OSP data as the terminal time is associated with the returned glove position. Once the microprocessor is able to retrieve the final OSP data, the initial time, and the terminal time, the present invention executes a single punch analysis to calculate the outputs of the present invention.

Figure 4:
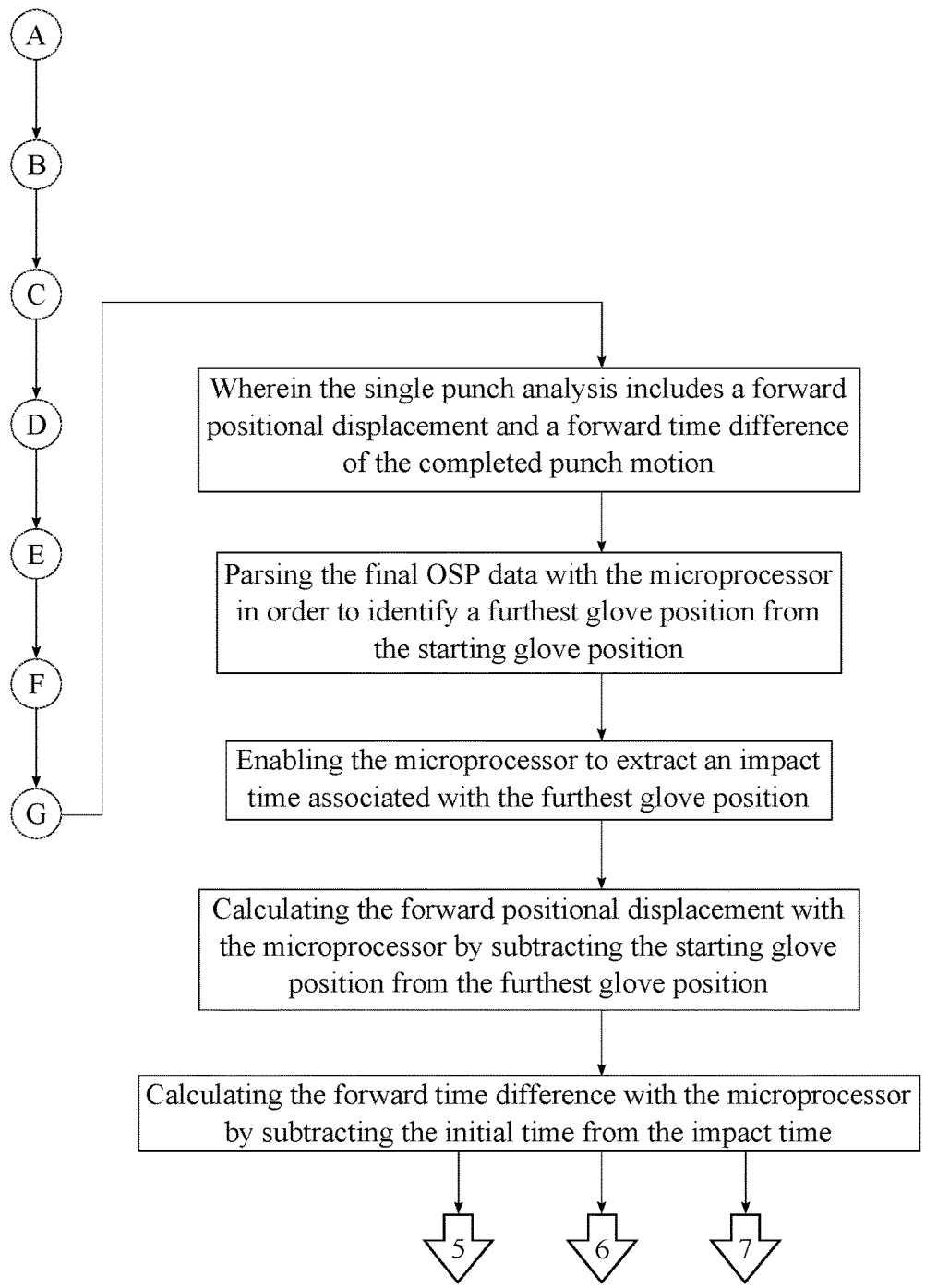
FIG. 4 is a flow chart illustrating the forward positional displacement and forward time difference calculations of the present invention within the overall process.

In reference to FIG. 2 and FIG. 4, when the single punch analysis is executed within the microprocessor, the present invention first calculates a forward positional displacement and a forward time difference of the completed punch motion. More specifically, the microprocessor parses the final OSP data in order to identify a furthest glove position from the starting glove position. The furthest glove position is recognized as the full or partial extension of the boxer's arm that simulates the punch. Then the microprocessor is able to extract an impact time from the final OSP data as the impact time associates with the furthest glove potion. Once the impact time is determined by the microprocessor, the present invention is able to calculate the forward positional displacement and the forward time difference. More specifically, the microprocessor subtracts the starting glove position from the furthest glove position to calculate the forward positional displacement while the initial time is subtracted from the impact time to calculate the forward time difference.

Figure 5:
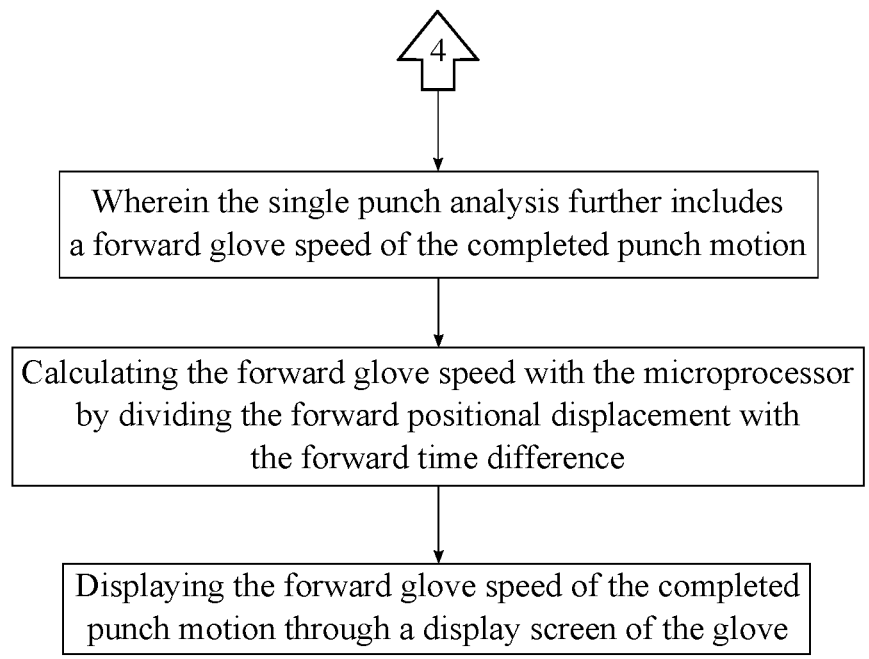
FIG. 5 is a flow chart illustrating the forward glove speed calculation of the present invention within the overall process.

In reference to FIG. 2, FIG. 4, and FIG. 5, a forward glove speed of the completed punch motion can be calculated through the single punch analysis so that the boxer is able to determine the forward glove speed of the punch through the present invention. More specifically, the microprocessor divides the forward positional displacement by the forward time difference so that the present invention is able to retrieve the forward glove speed. Then the forward glove speed for the completed punch motion can be displayed to the boxer through the display screen as an output of the single punch analysis.

Figure 6:
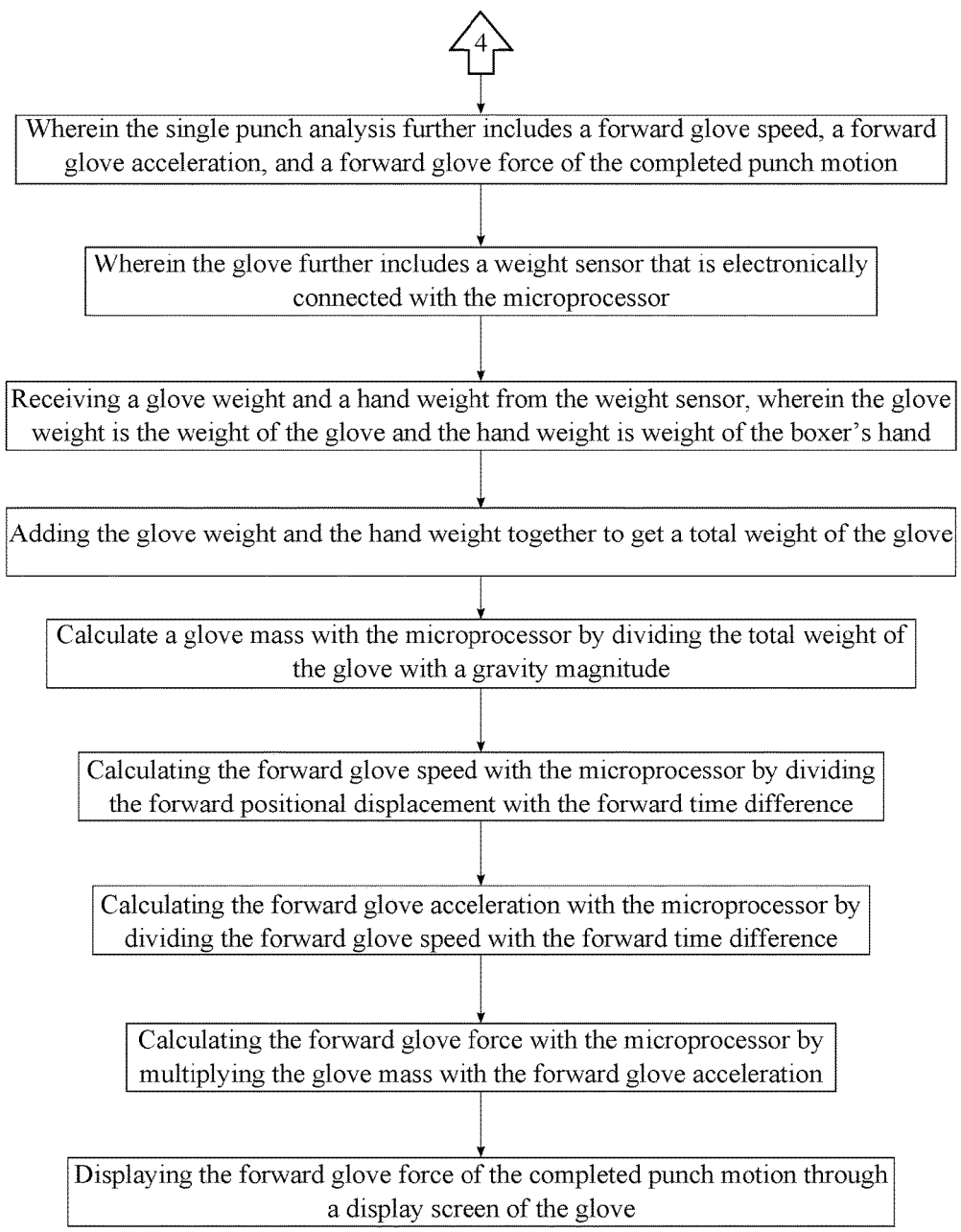
FIG. 6 is a flow chart illustrating the forward glove acceleration calculation of the present invention within the overall process.

In reference to FIG. 2, FIG. 4, and FIG. 6, a forward glove force of the completed punch motion can be calculated through the single punch analysis so that the boxer is able to determine the forward glove force of the punch through the present invention. In order to calculate the forward glove force, the microprocessor first calculates a total weight of the glove and the boxer's hand. More specifically, the microprocessor receives a glove weight and a hand weight from the weight sensor as the glove weight represents the weight of the glove and the hand weight represents the weight of the boxer's hand. Then the glove weight and the hand weight are added together to get the total weight of the glove. The microprocessor then divides the total weight of the glove with a gravity magnitude to calculate a glove mass. Once the mass of the glove is calculated within the present invention, the microprocessor then calculates the forward glove speed of the completed punch motion. Then the microprocessor is able to calculate a forward glove acceleration by dividing the forward glove speed with the forward time difference. After the glove mass and the forward glove acceleration are calculated, the microprocessor is able to calculate the forward glove force by multiplying the glove mass and the forward glove acceleration. Then the forward glove force for the completed punch motion can be displayed to the boxer through the display screen as an output of the single punch analysis.

Figure 7:
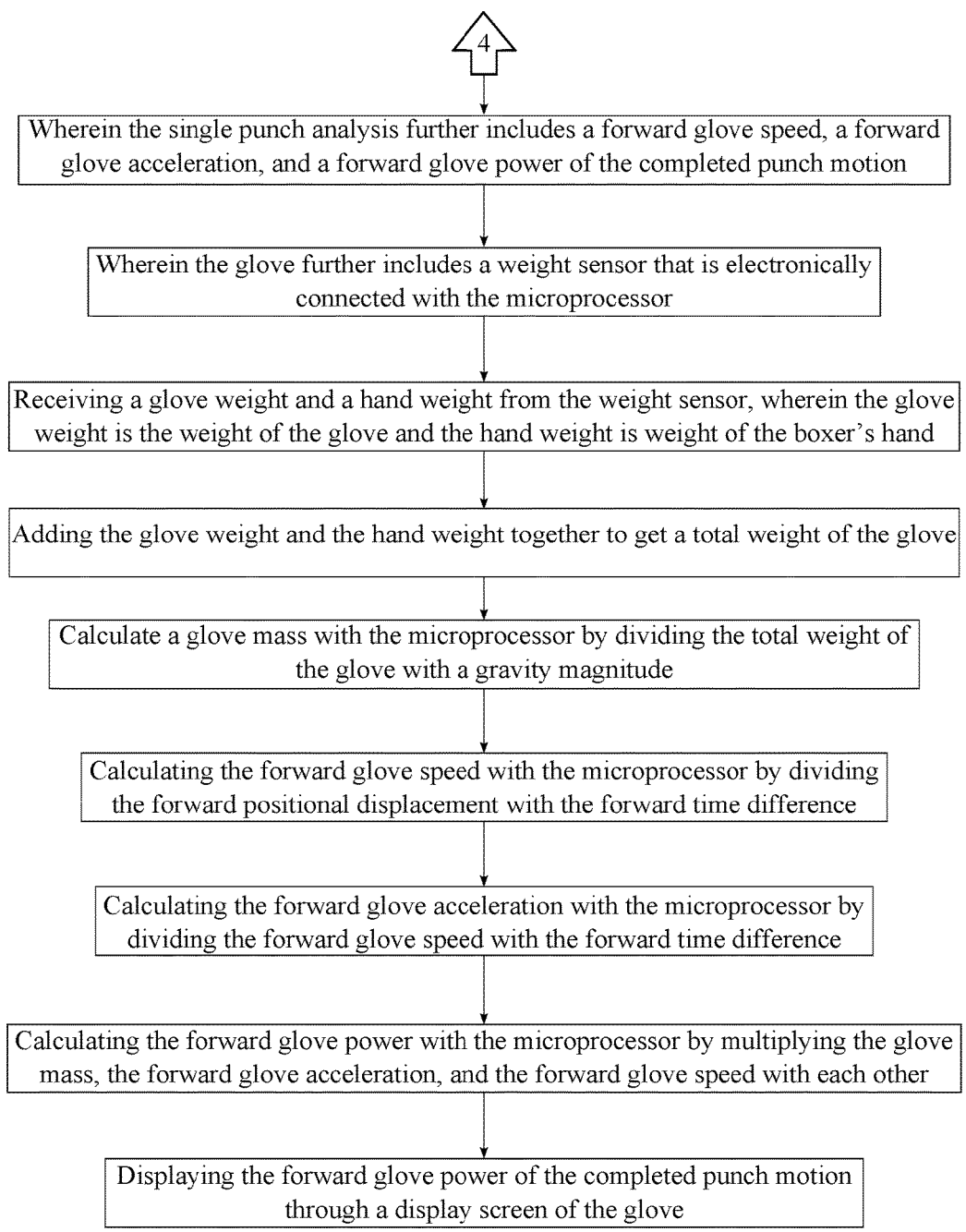
FIG. 7 is a flow chart illustrating the forward glove power calculation of the present invention within the overall process.

In reference to FIG. 2, FIG. 4, and FIG. 7, a forward glove power of the completed punch motion can be calculated through the single punch analysis so that the boxer is able to determine the forward glove force of the punch through the present invention. In order to calculate the forward glove force, the microprocessor first calculates the total weight of the glove, the glove mass, the forward glove speed, and the forward glove acceleration as explained above. Then the microprocessor is able to calculate the forward glove power through the aforementioned outputs. More specifically, the microprocessor multiplies the glove mass, the forward glove acceleration, and the forward glove speed with each other to calculate the forward glove power. Then the forward glove power for the completed punch motion can be displayed to the boxer through the display screen as an output of the single punch analysis.

Figure 8:
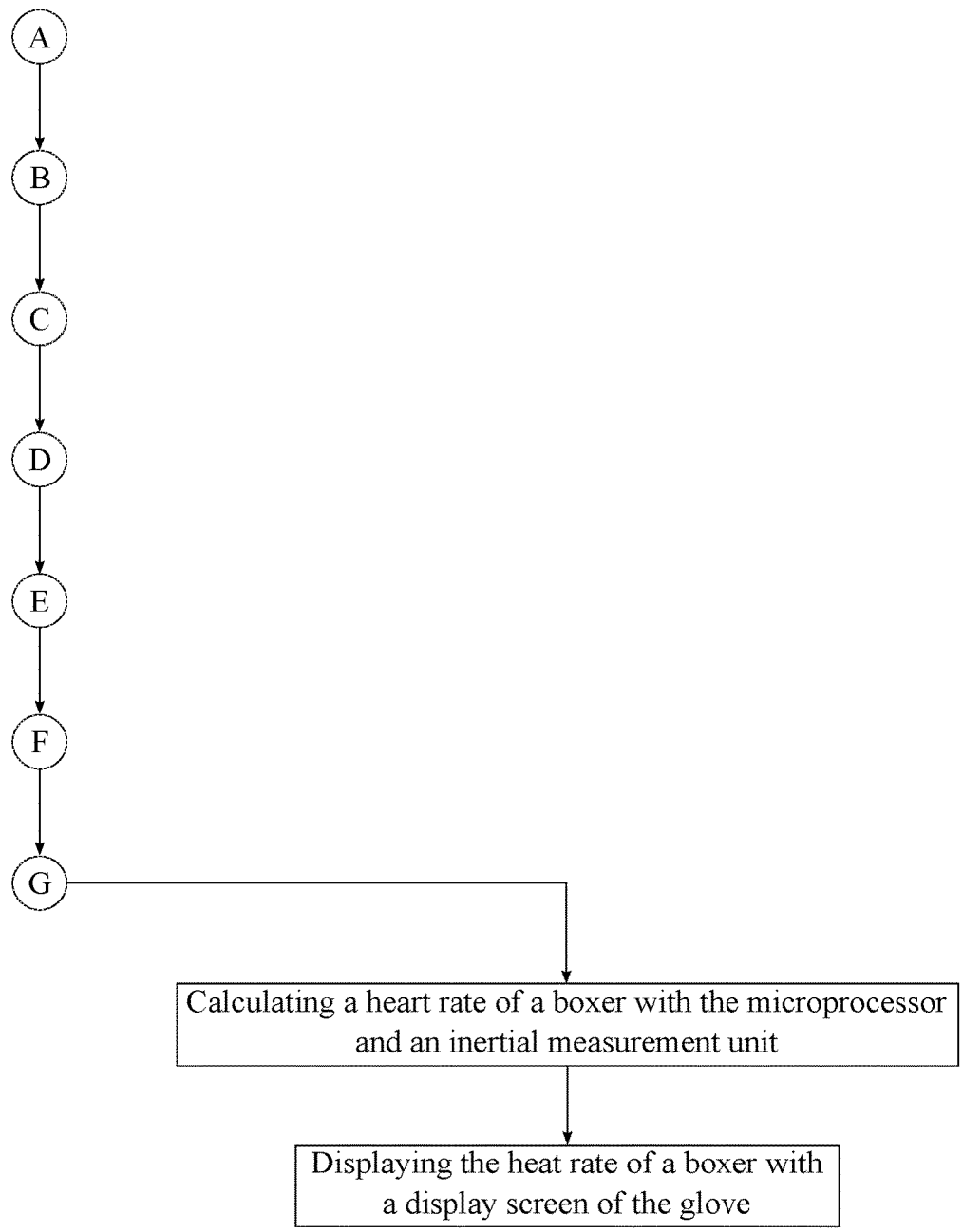
FIG. 8 is a flow chart illustrating the heart rate calculation of the present invention within the overall process.
Figure 9:
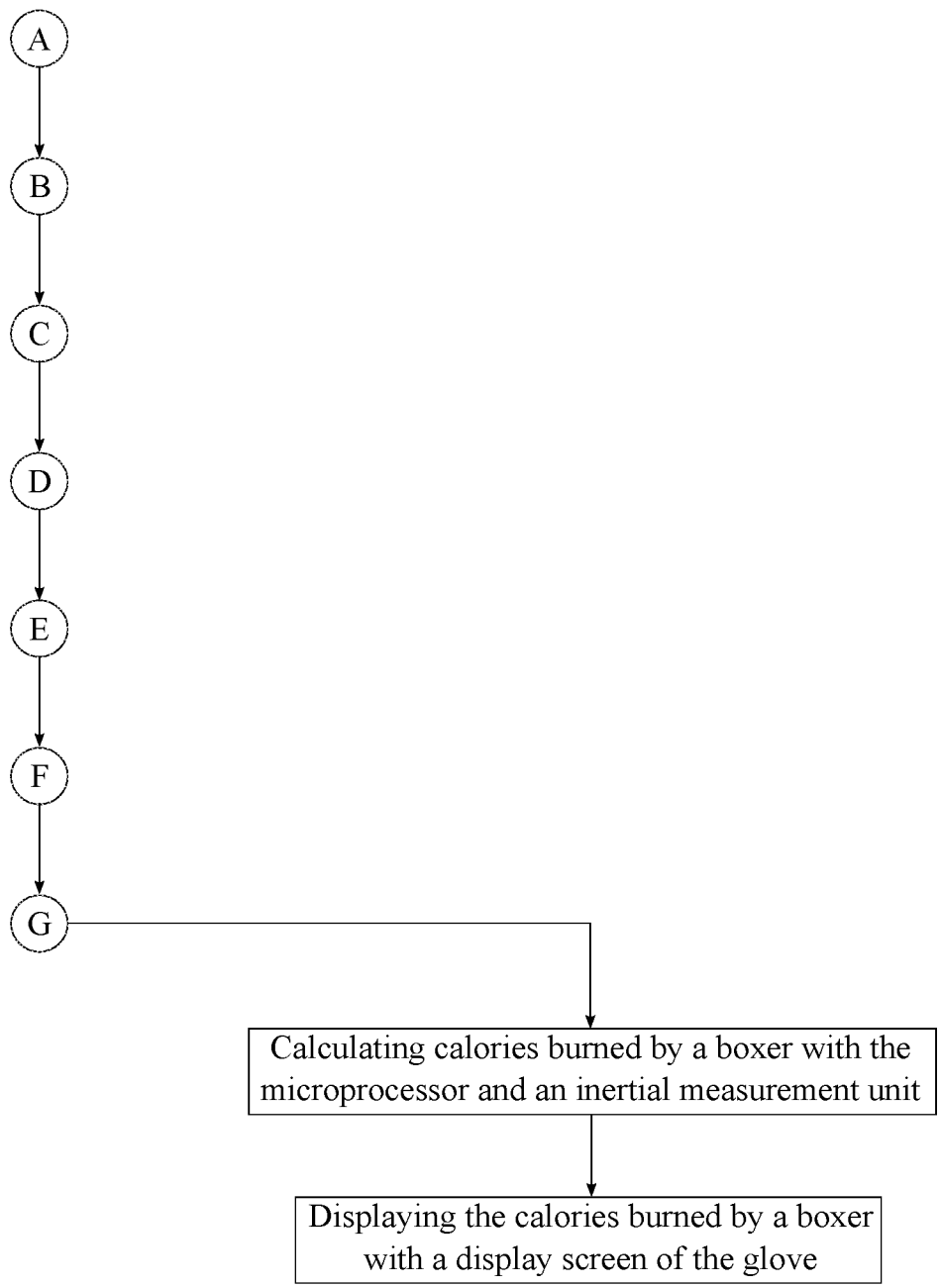
FIG. 9 is a flow chart illustrating the burned calories calculation of the present invention within the overall process.

In reference to FIG. 2, FIG. 8, and FIG. 9, the present invention also calculates a heart rate of the boxer and calories burned by the boxer through the microprocessor and the inertial measurement unit. The heart rate of the boxer and the calories burned by the boxer are displayed through the display screen so that the boxer is able to keep track of those parameters throughout the training session.

Figure 10:
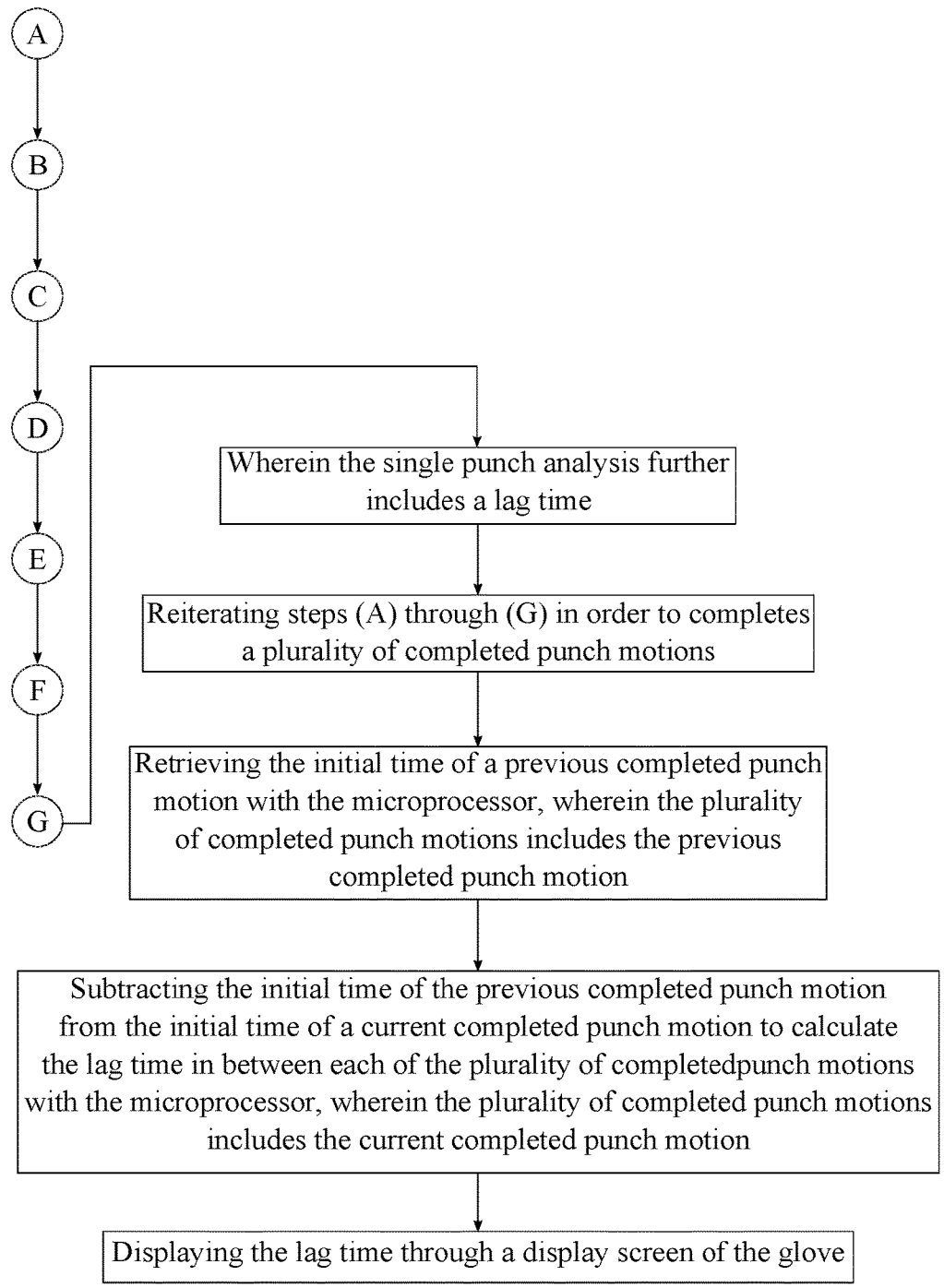
FIG. 10 is a flow chart illustrating the lag time calculation of the present invention within the overall process.

In reference to FIG. 2 and FIG. 10, when the glove is utilized for a plurality of completed punch motions, the present invention is able to calculate a lag time between each of the completed punch motions. More specifically, the microprocessor retrieves the initial time of a previous completed punch motion as the plurality of completed lunch motions includes the previous completed punch motion. Then the initial time of the previous completed punch is subtracted from the initial time of a current completed punch motion to calculate the lag time between each of the plurality of completed punch motions, wherein the plurality of completed punch motions includes the current completed punch motion. Then the lag time is displayed through the display screen as an output of the single punch analysis.

Figure 11:
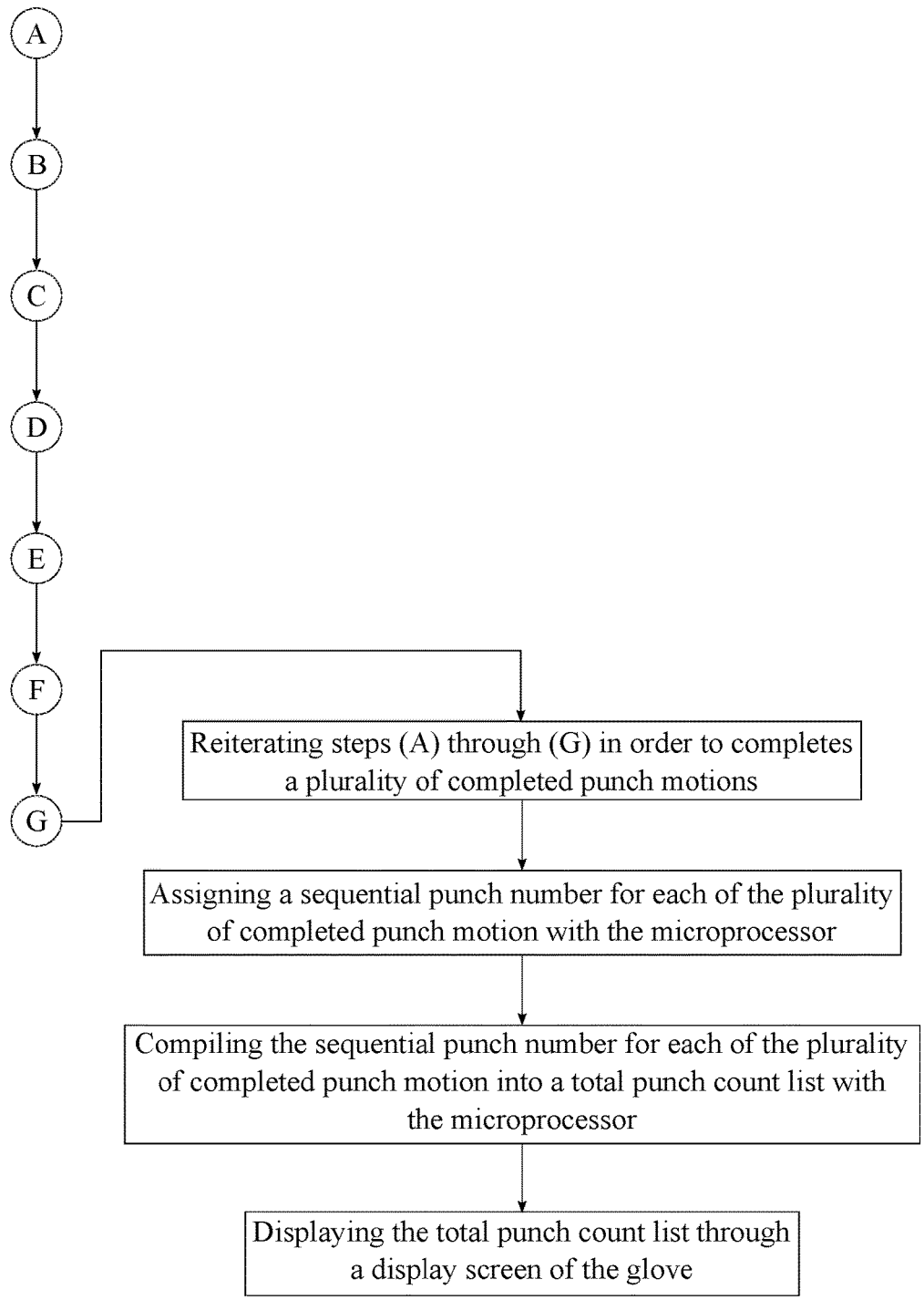
FIG. 11 is a flow chart illustrating the total punch count calculation of the present invention within the overall process.

In reference to FIG. 2 and FIG. 11, the microprocessor also keep track of a total punch count number throughout the training session. More specifically, the microprocessor continuously assigned a sequential punch number for each of the plurality of completed punch motion during the training session. Then the sequential punch number is continuously complied into a total punch count list with the microprocessor as the compiled total punch count is displayed to the boxer through the display screen. Then the boxer is able to separately analysis each of the completed punch motion with respect the forward glove speed, the forward glove force, the forward glove power, the heart rate of the boxer, the calories burned by the boxer, and the lag time between consecutive punches.

Figure 12:
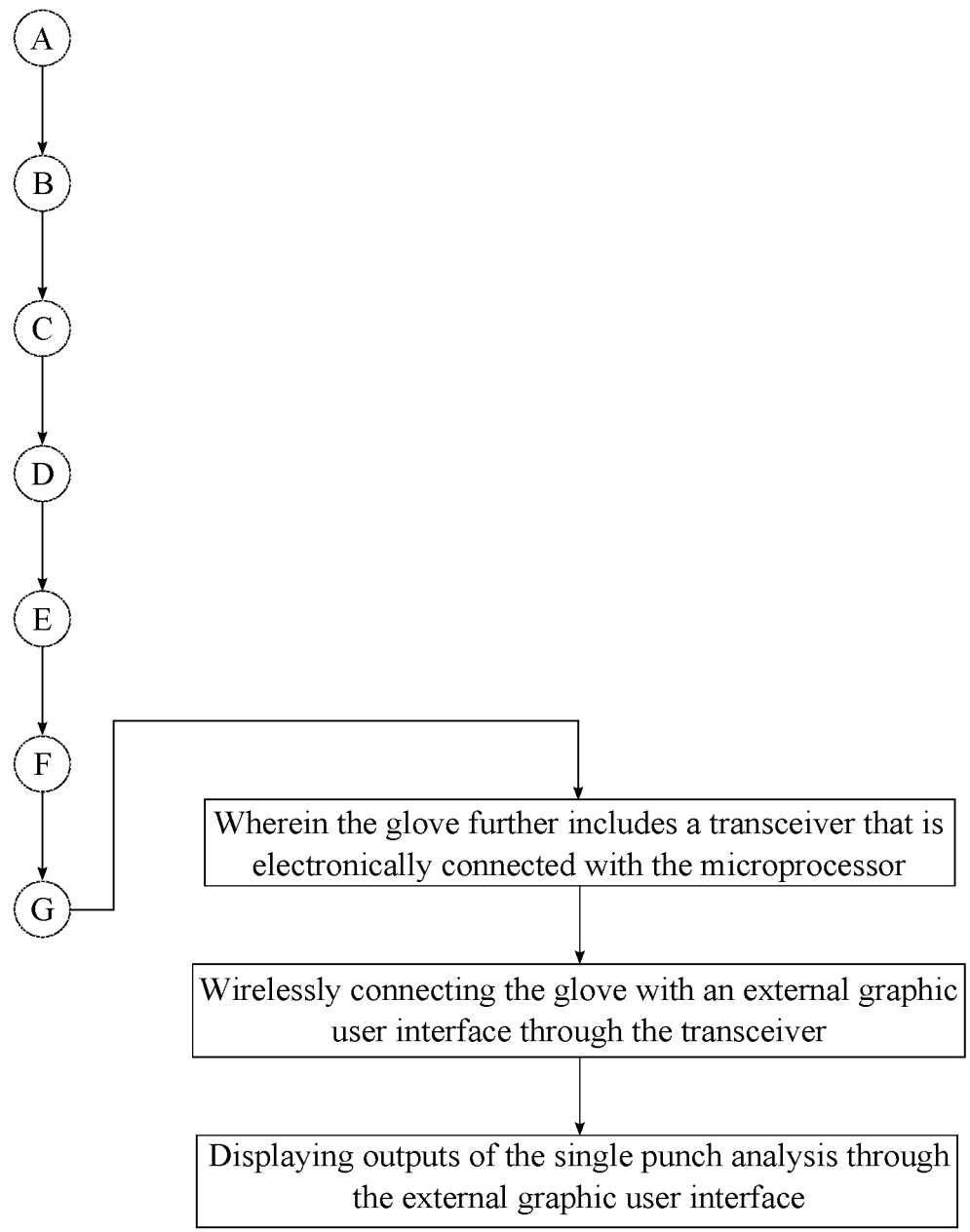
FIG. 12 is a flow chart illustrating the electronical connection for the external graphic user interface of the present invention within the overall process.

In reference to FIG. 2 and FIG. 12, the glove further comprises a transceiver that is electronically connected with the microprocessor. The transceiver wirelessly connects the glove with an external graphic user interface so that the microprocessor is able to display the outputs through the graphic user interface and the display screen. In order to wirelessly connect with the glove, the graphic user interface may require a mobile application that is compatible to operate with the present invention.

Although the invention has been explained in relation to its preferred embodiment, it is to be understood that many other possible modifications and variations can be made without departing from the spirit and scope of the invention as hereinafter claimed.

What is claimed is:

1. A method of analyzing punching activities of a boxer during a training session comprises the steps of:
    (A) providing at least one glove, wherein the glove includes a microprocessor, an inertial measurement unit, and a power source;
    (B) timestamping and collecting raw orientation and spatial positioning (OSP) data from the inertial measurement unit;
    (C) identifying a starting glove position amongst the raw OSP data with the microprocessor;
    (D) parsing the raw OSP data with the microprocessor in order to identify a returned glove position amongst the raw OSP data, wherein the returned glove position matches the starting glove position;
    (E) enabling the microprocessor to designate a subset from the raw OSP data between the starting glove position and the returned glove position as final OSP data of a completed punch motion;
    (F) enabling the microprocessor to extract an initial time associated with the starting glove position and a terminal time associated with the returned glove position;
    (G) executing a single punch analysis with the microprocessor, wherein the final OSP data, the initial time, and the terminal time are inputs for the single punch analysis;
    calculating a heart rate of the boxer with the microprocessor and the inertial measurement unit; and
    displaying the heat rate of the boxer with a display screen of the glove.

2. The method of analyzing punching activities of a boxer during a training session, the method as claimed in claim 1,
    wherein the microprocessor and the inertial measurement unit are electronically connected with each other; and
    wherein the microprocessor and the inertial measurement unit are electrically connected with the power source.

3. The method of analyzing punching activities of a boxer during a training session, the method as claimed in claim 1 comprises the steps of:
    wherein the single punch analysis includes a forward positional displacement and a forward time difference of the completed punch motion;
    parsing the final OSP data with the microprocessor in order to identify a furthest glove position from the starting glove position;
    enabling the microprocessor to extract an impact time associated with the furthest glove position;
    calculating the forward positional displacement with the microprocessor by subtracting the starting glove position from the furthest glove position; and
    calculating the forward time difference with the microprocessor by subtracting the initial time from the impact time.

4. The method of analyzing punching activities of a boxer during a training session, the method as claimed in claim 3 comprises the steps of:
    wherein the single punch analysis further includes a forward glove speed of the completed punch motion;
    calculating the forward glove speed with the microprocessor by dividing the forward positional displacement with the forward time difference; and
    displaying the forward glove speed of the completed punch motion through the display screen of the glove.

5. The method of analyzing punching activities of a boxer during a training session, the method as claimed in claim 3 comprises the steps of:
    wherein the single punch analysis further includes a forward glove speed, a forward glove acceleration, and a forward glove force of the completed punch motion;
    wherein the glove further includes a weight sensor that is electronically connected with the microprocessor;
    receiving a glove weight and a hand weight from the weight sensor, wherein the glove weight is the weight of the glove and the hand weight is weight of the boxer's hand;
    adding the glove weight and the hand weight together to get a total weight of the glove;
    calculate a glove mass with the microprocessor by dividing the total weight of the glove with a gravity magnitude;
    calculating the forward glove speed with the microprocessor by dividing the forward positional displacement with the forward time difference;
    calculating the forward glove acceleration with the microprocessor by dividing the forward glove speed with the forward time difference;
    calculating the forward glove force with the microprocessor by multiplying the glove mass with the forward glove acceleration; and
    displaying the forward glove force of the completed punch motion through a the display screen of the glove.

6. The method of analyzing punching activities of a boxer during a training session, the method as claimed in claim 3 comprises the steps of:
    wherein the single punch analysis further includes a forward glove speed, a forward glove acceleration, and a forward glove power of the completed punch motion;
    wherein the glove further includes a weight sensor that is electronically connected with the microprocessor;
    receiving a glove weight and a hand weight from the weight sensor, wherein the glove weight is the weight of the glove and the hand weight is weight of the boxer's hand;
    adding the glove weight and the hand weight together to get a total weight of the glove;
    calculate a glove mass with the microprocessor by dividing the total weight of the glove with a gravity magnitude;
    calculating the forward glove speed with the microprocessor by dividing the forward positional displacement with the forward time difference;
    calculating the forward glove acceleration with the microprocessor by dividing the forward glove speed with the forward time difference;
    calculating the forward glove power with the microprocessor by multiplying the glove mass, the forward glove acceleration, and the forward glove speed with each other; and
    displaying the forward glove power of the completed punch motion through the display screen of the glove.

7. The method of analyzing punching activities of a boxer during a training session as claimed in claim 1 comprises the steps of:
    calculating calories burned by the boxer with the microprocessor and the inertial measurement unit; and displaying the calories burned by the boxer with the display screen of the glove.

8. The method of analyzing punching activities of a boxer during a training session as claimed in claim 1 comprises the steps of;
wherein the single punch analysis further includes a lag time;
reiterating steps (A) through (G) in order to completes a plurality of completed punch motions;
retrieving the initial time of a previous completed punch motion with the microprocessor, wherein the plurality of completed punch motions includes the previous completed punch motion;
subtracting the initial time of the previous completed punch motion from the initial time of a current completed punch motion to calculate the lag time in between each of the plurality of completed punch motions with the microprocessor, wherein the plurality of completed punch motions includes the current completed punch motion; and
displaying the lag time through the display screen of the glove.

9. The method of analyzing punching activities of a boxer during a training session as claimed in claim 1 comprises the steps of;
reiterating steps (A) through (G) in order to completes a plurality of completed punch motions;
assigning a sequential punch number for each of the plurality of completed punch motion with the microprocessor;
compiling the sequential punch number for each of the plurality of completed punch motion into a total punch count list with the microprocessor; and
displaying the total punch count list through the display screen of the glove.

10. The method of analyzing punching activities of a boxer during a training session as claimed in claim 1 comprises the steps of:
wherein the glove further includes a transceiver that is electronically connected with the microprocessor;
wirelessly connecting the glove with an external graphic user interface through the transceiver; and
displaying outputs of the single punch analysis through the external graphic user interface.

* * * * *